United States Patent [19]

De Meere et al.

[11] Patent Number: 5,384,132

[45] Date of Patent: Jan. 24, 1995

[54] STABILIZED GONADOTROPIN CONTAINING PREPARATIONS

[75] Inventors: Andreas L. J. De Meere, Waspik; Marinus A. De Ruiter, Oss, both of Netherlands

[73] Assignee: Akzo N.V., Arnhem, Netherlands

[21] Appl. No.: 116,420

[22] Filed: Sep. 3, 1993

Related U.S. Application Data

[60] Division of Ser. No. 914,227, Jul. 13, 1992, Pat. No. 5,270,057, which is a continuation of Ser. No. 672,509, Mar. 20, 1991, abandoned.

[30] Foreign Application Priority Data

Mar. 20, 1990 [EP] European Pat. Off. .......... 90200665

[51] Int. Cl.$^6$ .......................... A61K 9/14; A61K 37/38
[52] U.S. Cl. .......................... 424/499; 514/2; 514/8; 514/21; 514/23; 530/398; 530/399; 530/852
[58] Field of Search ............ 424/499; 514/2, 8, 21, 514/23; 530/398, 399, 850–853

[56] References Cited

U.S. PATENT DOCUMENTS

| | | | |
|---|---|---|---|
| 3,932,943 | 1/1976 | Briggs et al. | 34/5 |
| 4,062,942 | 12/1977 | Donini et al. | 424/100 |
| 4,457,916 | 7/1984 | Hayashi et al. | 424/101 |
| 4,478,829 | 10/1984 | Landaburu et al. | 424/177 |
| 4,623,717 | 11/1986 | Fernandes et al. | 530/380 |
| 4,806,524 | 2/1989 | Kawaguchi et al. | 514/8 |
| 4,812,557 | 3/1989 | Yashushi et al. | 530/351 |
| 4,816,568 | 3/1989 | Hamilton, Jr. et al. | 530/399 |
| 4,824,938 | 4/1989 | Koyama et al. | 530/351 |

FOREIGN PATENT DOCUMENTS

| | | |
|---|---|---|
| 098073 | 1/1984 | European Pat. Off. . |
| 302772 | 2/1989 | European Pat. Off. . |
| 303746 | 2/1989 | European Pat. Off. . |
| 5925333 | 2/1984 | Japan . |
| WO87/0053-00 | 9/1987 | WIPO . |

OTHER PUBLICATIONS

*Research Disclosure,* No. 169, pp. 4–6, May 1978, Havant GB.

*Primary Examiner*—G. S. Kishore
*Attorney, Agent, or Firm*—William M. Blackstone; Mary E. Gormley

[57] ABSTRACT

Disclosed are lyophilized gonadotropin containing preparations containing a dicarboxylic acid salt stabilizer. The particular proteins (e.g. LH, TSH, FSH, or HCG) are in admixture with, and at least partially capable of stabilization by, the particular stabilizer in lyophilized form. The preparations contain a sufficient amount of dicarboxylic acid salt to stabilize the protein in freeze-dried form for a desired time at a desired temperature. Typical dicarboxylic acid salts disclosed are the salts of citric, tartaric, and aspartic acids. The preparations preferably include a non-reducing disaccharide to increase the collapse temperature of the solution to be lyophilized. Methods of making the preparations in lyophilized form and the resulting injectable preparations are also disclosed.

6 Claims, 2 Drawing Sheets

STABILIZED GONADOTROPIN CONTAINING PREPARATIONS

This is a division, of application Ser. No. 07/914,227 filed Jul. 13, 1992, now U.S. Pat. No. 5,270,057, which is a file wrapper continuation of U.S. Ser. No. 07/672,509, filed Mar. 20, 1991, now abandoned.

BACKGROUND OF THE INVENTION

1. Field. This invention relates to pharmaceutical compositions generally, and to stabilized gonadotropin containing preparations specifically.

2. State of the Art: Relatively pure gonadotropin preparations are commercially available. For example, compositions containing naturally derived human menopausal gonadotropin ("HMG") and naturally derived human chorionic gonadotropin ("HCG") are available as freeze-dried preparations under the trade designations "Humegon" and "Pregnyl," respectively, from Organon International, bv of Oss, NL. Pregnant mare gonadotropin is also available in a freeze dried form from the same company.

A bulking agent, e.g. mannitol, is added to these preparations before lyophilization. They do not require the addition of a stabilizer to ensure an adequate shelf-life. Evidently whatever natural contaminants remain after the purification process act to stabilize the preparations in freeze-dried form.

Recently however, with the advent of more effective production and purification techniques, preparations of certain very pure gonadotropins are insufficiently stable. They degrade in a relatively short time, losing activity. In order to prevent or slow down this degradation, attempts were made to freeze-dry (lyophilize) the preparations. Lyophilization has only been partially successful however.

A need exists for a gonadotropin containing pharmaceutical preparation which is stable over a sufficiently long period of time for the product to be manufactured, shipped, and stored prior to use. The need is especially great for a stable preparation containing more than one gonadotropin.

SUMMARY OF THE INVENTION

Generally, the invention includes a gonadotropin containing lyophilized protein preparation which contains a dicarboxylic acid salt stabilizer. "Dicarboxylic acid," as used herein, means an organic acid having two or more carboxylic acid moieties (e.g. HOOC—R—COOH). The gonadotropin will be in admixture with, and at least partially capable of stabilization by, the particular stabilizer in lyophilized systems. The preparation will contain a sufficient amount of dicarboxylic acid salt to stabilize the gonadotropin in its freeze-dried form for a desired time at a desired temperature.

Typical dicarboxylic acid salts are salts of citric acid, tartaric acid, aspartic acid, or mixtures of these acids. The gonadotropin or gonadotropin derivatives (as used herein "gonadotropins") will typically be proteins such as follicle stimulating hormone (FSH), thyroid stimulating hormone (TSH), human chorionic gonadotropin (HCG), or luteinizing hormone (LH). The preparation can further include a non-reducing disaccharide, such as sucrose or trehalose.

The invention also includes a method of stabilizing an essentially pure gonadotropin, in lyophilized form, which method involves mixing the gonadotropin, in solution, with a sufficient amount of a dicarboxylic acid salt to stabilize the protein in the lyophilized form, and then freeze-drying the resulting solution to form a stabilized lyophilisate of the gonadotropin.

The invention further includes the reconstituted injectable preparation made from the lyophilisate. The injectable preparation consists essentially of aqueous solution of water for injection, the gonadotropin, a non-reducing sugar, an anti-adsorption agent, and the dicarboxylic acid salt.

DESCRIPTION OF THE PREFERRED EMBODIMENTS

A. Gonadotropins

Figure 1:
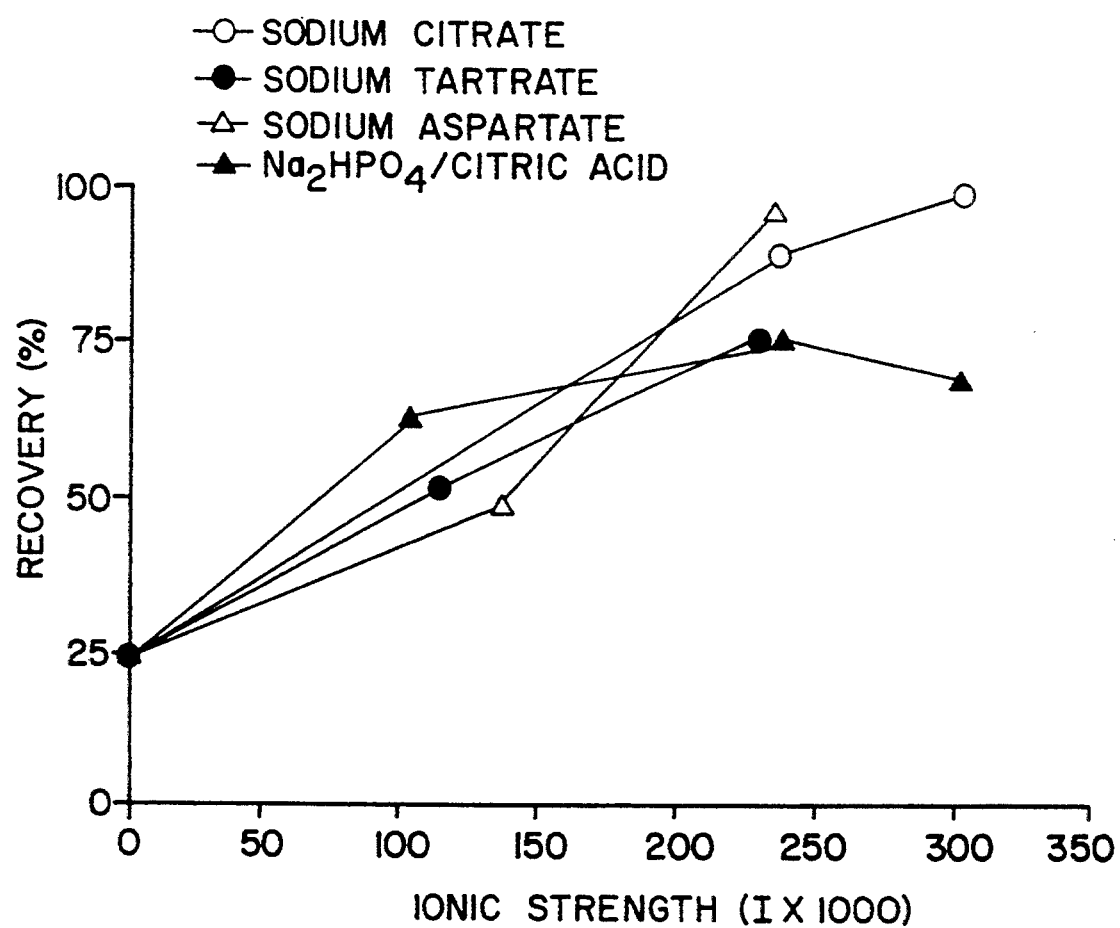
FIG. 1 is a graph depicting the correlation between ionic strength (X 1000) versus the amount of recovery of recombinant FSH activity after 1 month at 60° C. using various stabilizers.

Preferred gonadotropins are FSH, TSH, HCG, LH, derivatives and mixtures thereof, with or without other protein components. Follicle stimulating hormone, thyroid stimulating hormone, human chorionic gonadotropin, and luteinizing hormone are all chemically related proteins which consist of $\alpha$ and $\beta$ subunits. The $\alpha$ subunits of these proteins are identical or nearly so.

Follicle stimulating hormone is a hormonal glycoprotein of the anterior pituitary required for normal reproductive function. Follicle stimulating hormone has been used to stimulate development of ovarian follicles for in vitro fertilization, and has also been used clinically to stimulate follicular maturation in anovulatory women with chronic anovulatory syndrome or luteal phase deficiency. Follicle stimulating hormone may be at least partially isolated from natural sources, such as human urine. Recombinant follicle stimulating hormone and/or LH may be prepared as described in Keene et al "Expression of Biologically Active Human Follitropin in Chinese Hamster Ovary Cells," *The Journal of Biological Chemistry*, Vol. 264, pp. 4769–4775 (Mar, 25, 1989), the contents of which are incorporated by this reference. As used herein, a gonadotrophin, for example follicle stimulating hormone (FSH), includes the compound's analogs, and its recombinant, natural, deglycosylated, unglycosylated, modified glycosylated, and other forms.

The most preferred gonadotropin is FSH produced by recombinant DNA techniques (rFSH), either alone or in a lyophilisate with LH or HCG. FSH purified from natural sources is generally only partially purified. The impurities seem to act to stabilize it somewhat. With rFSH, however the impurities are not present, and thus the FSH is more susceptible to rapid degradation and freeze-drying losses. Doses of FSH range from 60 to 1500, especially 75 to 225 IU per ampoule lyophilisate.

Any gonadotropin used is preferably present in the lyophilisate preparations in a quantity sufficient to form a therapeutically useful concentration of the protein after dilution, generally for parenteral (e.g. subcutaneous or intravenous) administration, with a specified amount of an aqueous solution (e.g. distilled water for injection or sterile normal saline) to form a volume of preparation contemplated for use. As used herein, an aqueous solution is a solution containing water as a primary, but not necessarily the only, solvent. For example, a container containing FSH may contain 1 to 1000 micrograms (μg) of FSH (e.g. 75 international units is considered a therapeutic amount). Preferably, the highest reasonable amount of protein possible will be present in a container, since the greater the amount of protein present, generally the more stable the preparation. Useful doses of gonadotropins are known to medical practitioners, and the amount included in a dose is generally dependent upon the disease state and the particular patient being treated.

Illustratively, amounts as high as 10,000 international units and as low as 15 international units of HCG have been administered. Injections ranging from 20 to 225 international units LH have been used.

In one preferred embodiment, a combination of FSH and LH or FSH and HCG are lyophilised together to from a preparation having therapeutic amounts of both of the selected gonadotropins.

B. Stabilizers

As used herein, "stabilize" is a relative term. To stabilize with a stabilizing agent or compound means the ability to prevent or delay a decrease in the protein's activity with the stabilizing agent. For example, a preparation would be deemed "stabilized" if, with the addition of a stabilizing compound ("stabilizer"), it took longer (e.g. 2 weeks instead of 1 week) to degrade at a set temperature, thus losing some of its in vivo or in vitro activity in comparison to the preparation sans the stabilizer.

A protein's activity may be determined by known methods relating to the particular protein. One measure of activity can be made by measuring the amount of (inactive) oligomers formed over time. Oligomer formation in a sample can be determined by HPSEC.

Other methods of determining the residual activity of, for example, rFSH include enzyme immunoactivity assay ("EIA") as described in U.S. Pat. No. Re. 32,696 to Schuurs et al; a kit available under the trade designation "FSHEIA" from bioMérieux of Marcy l'Etoile 69260 Charbonnières-les-Bains, France for FSH; and in vitro bioassay of both FSH and LH as described in Mannaerts et al, "Applications of in vitro Bioassays for Gonadotropins," *Neuroendocrinology of Reproduction*, pp. 49-58 (Elsevier Science Publishers bv, Amsterdam, NL 1987).

Preferred stabilizers for use with the preparations are salts of dicarboxylic acids such as citric acid, tartaric acid, aspartic acid, and mixtures thereof. Preferred salts are the sodium, potassium, lithium and ammonium salts of such dicarboxylic acids, especially sodium and potassium salts. Another dicarboxylic acid salt is sodium glutamate. The presence of a dicarboxylic acid salt stabilizer acts to stabilize the enzymatic mixtures, especially at relatively higher temperatures over longer periods of time.

When used as stabilizers, aspartate and glutamate salts gave better recovery of activity than did citrate, isocitrate, or tartrate salts.

When a citrate salt is the selected stabilizer, a ratio of citrate to gonadotropin in the range of 200 to 400 (mg/mg) is preferred, giving the best stabilization and recovery in the presence of some sugar. An especially preferred protein for use with sodium citrate is rFSH, due to the compound's ability to be stabilized with the stabilizer.

Concentrations of dicarboxylic acid salt stabilizers sufficient to form a solution having an ionic strength of greater than 0.050 are preferred in FSH compositions containing between 0.1 and 1000 μg of FSH. Especially preferred are those solutions having an ionic strength of between 0.250 and 0.350 which will generally stabilize, for example, rFSH stored at one month at 60° C. to yield a 75% recovery of rFSH. Calculation of ionic strength is well-known to those skilled in the art, for example see Chase, et al, *Remington's Pharmaceutical Sciences*, pp. 223-224, 228, and 233 (16th ed. 1980, Mack Publ. Co. of Easton, Pa., U.S.A.).

Concentrations of 2.5 to 17.5 milligrams per milliliter (mg/ml) of sodium citrate in solution are generally sufficient to stabilize lyophilized rFSH in the amounts described herein.

Figure 2:
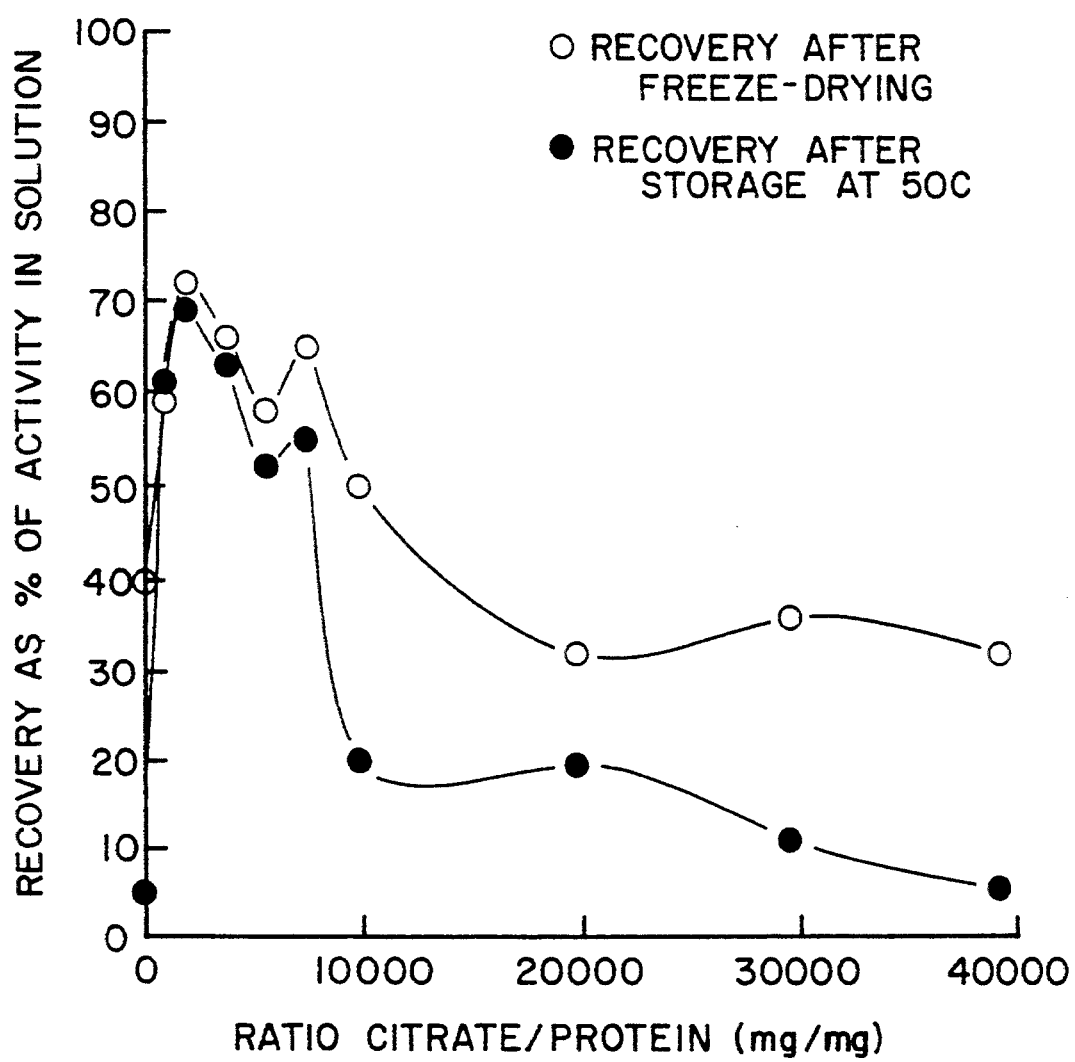
FIG. 2 is a graph depicting the effect of citrate/protein ratio (weight/weight) on recovery of HCG activity.

Also as depicted in FIG. 2, citrate should be present in a composition with, for example, HCG in an amount less than 10,000 times by weight that of the HCG to achieve greater stability.

C. Non-reducing Sugars

The compositions to be freeze-dried preferably contain a non-reducing sugar such as sucrose or trehalose. The incorporation of such a sugar, e.g. sucrose, acts to increase the "collapse (or 'shrinkage') temperature" at which the lyophilization of the solution takes place. This increase in temperature simplifies the entire freeze-drying process. An especially preferred non-reducing sugar for this use is sucrose in its amorphic state.

The amount of non-reducing sugar present in the solution to be lyophilized will generally be dependent upon the amount of dicarboxylic acid salt stabilizer present. For example, the weight ratio of non-reducing sugar to dicarboxylic acid salt will generally vary between 50:1 to 10:3 with a preferred concentration being about 3.3:1 in the case of sucrose to sodium citrate. Especially preferred is a solution containing 50 mg/ml sucrose and 14.7 mg/ml sodium citrate which also yields an optimal lyophilisate in terms of physical characteristics.

In the presently most preferred embodiments, the amount of sucrose will be sufficient to raise the collapse temperature from $-38°$ C. to about $-25°$ C. as determined by differential scanning calorimetry. The resulting lyophilisate "cake" remains amorphous and stable for relatively longer periods of time.

D. Anti-absorption agents

Anti-adsorption agents are preferably added to the lyophilized composition to prevent adsorbance of the protein to the walls of the container in which the compositions are contained, thus preventing a possible decrease in concentration. Certain anti-adsorption agents (e.g. polysorbates) also act as "cryoprotectants" protecting the protein during the lyophilization process.

Preferred anti-adsorption agents are nonionic surfactants such as Polysorbate 20, NF (Tween 20 available from Atlas Chemical Company), Polysorbate 80, NF (Tween 80 available from Atlas Chemical Company), Brij 35 (available from ICI Pharmaceuticals of Great Britain), and Pluronic F123 (available from BASF of Ludwigshafen, W. Germany). Polysorbate 20, NF is especially preferred.

Polysorbate is preferably understood as meaning a polysorbate which meets the specification of USP/NF XXII, which is published as "*The National Formulary*", p. 1763 and 1967, Official from Jan. 1, 1990 (22nd ed., U.S. Pharmacopeial Convention, Inc. 1989).

An anti-adsorption agent or anti-adsorption agents will be present in such amounts that adsorption of the protein onto container walls, or walls of vessels during processing, is decreased. Illustratively, amounts of Polysorbate 20 sufficient to form a concentration between 0.1 and 0.2 mg/ml in the ultimate solution for use are preferred. Concentrations higher than this tend to lead to oligomer formation, and thus decreased activity.

E. Pharmaceutical Compositions

The stable lyophilized preparation of the instant invention can be prepared by admixing the selected protein in aqueous solution with a sufficient amount of a dicarboxylic acid salt stabilizer to stabilize the protein, and a sufficient amount of a non-reducing sugar to increase the collapse temperature from $-38°$ C. to greater than $-25°$ C. Temperatures greater than $-35°$ C. are preferred. Optionally, the selected anti-adsorption agent may also be added. The solution is then filtered, placed into containers (e.g. one ml glass ampoules) and then freeze-dried to form a stabilized lyophilisate. Freeze-drying techniques are well-known to those of skill in the art. For more information, reference may be made to several texts, including Goldblith et al, *Freeze Drying and Advanced Food Technology*, (Academic Press, Inc., London, GB 1975). Preferred residual water content in the lyophilisate cakes are between 1 and 5%. Aseptic techniques should be used throughout the procedure. Freeze-driers are available from manufacturers such as Leybold or Edwards. Using such a procedure, or modifications thereof, several different compositions may be prepared.

An especially preferred composition contains rFSH in admixture with a stabilizer which is a salt of a dicarboxylic acid, wherein the dicarboxylic acid is selected from the group consisting of citric acid, tartaric acid, aspartic acid, and mixtures of these acids.

Another preferred lyophilized preparation contains, in admixture, a dicarboxylic acid salt stabilizer, a gonadotropin capable of stabilization by the amount of stabilizer present in the preparation, and trehalose. This preparation further include sodium biphosphate in admixture with the stabilizer, protein, and non-reducing sugar. Especially preferred salts for such preparations are sodium aspartate, sodium citrate, and sodium tartrate.

Another preferred stable lyophilized preparation contains, in admixture, a stabilizer such as a salt of tartaric or aspartic acid, a gonadotropin capable of stabilization by the amount of stabilizer present in the preparation, and a non-reducing sugar. The preparation may further include disodium biphosphate in admixture with the stabilizer, protein, and non-reducing sugar. Especially preferred non-reducing sugars are trehalose and sucrose. An especially preferred stabilizer in such preparations is sodium aspartate.

Another highly preferred stabilized lyophilisate consists essentially of a protein; a sufficient amount of a dicarboxylic acid salt stabilizer to stabilize the protein in freeze dried form; a disaccharidic non-reducing sugar; an anti-adsorption agent to prevent said protein from adsorbing onto a container containing the lyophilisate; and less than five percent residual water. In such a lyophilisate the protein will be FSH; the dicarboxylic acid salt stabilizer will be selected from the group consisting of salts of citric acid, tartaric acid, and aspartic acid; the disaccharidic non-reducing sugar will either be sucrose or trehalose, and the anti-adsorption agent will be selected from the group consisting of Tween 20, Tween 80, Brij, or pluronic acid. This lyophilisate is especially preferred since, among other things, it has been discovered that the addition of further "stabilizers," such as mannitol, maltose, or either of them actually act to destabilize the lyophilisate in terms of activity.

Methods for making parenteral preparations and intravenous admixtures are disclosed in *Remington's Pharmaceutical Sciences*, pp. 1463–1497. However, caution must be exercised since although the stabilized compositions are compatible with infusion liquids, the infusion liquid used preferably should not contain reducing sugars. The preferred pH of the resulting solution for use should be between 6 and 8, especially 7.

The invention is further explained by reference to the following EXAMPLES:

EXAMPLE I

A. Stabilization of rFSH utilizing various disaccharides

Aqueous solutions containing 150 units of rFSH were prepared. The solutions were divided into three groups and each group was mixed with (1) 50 mg/ml maltose/14.7 mg/ml sodium citrate; (2) 50 mg/ml trehalose/14.7 mg/ml sodium citrate and (3) 50 mg/ml sucrose/14.7 mg/ml sodium citrate. All three solutions also contained 0.2 mg/ml Polysorbate 20, NF. The three groups of solutions were freeze-dried, and the resulting lyophilisate allowed to sit for four weeks at 60° C. The lyophilisates were then tested for activity (as determined by EIA) with the following results:

| Compound: | (1) | (2) | (3) |
|---|---|---|---|
| Percentage activity: | 40% | 89% | 87% |

This EXAMPLE shows that non-reducing disaccharides aid stability better than reducing disaccharides.

B. Stabilization of rFSH with Sodium Citrate

Two lyophilized samples are made. The first sample contains 75 Units rFSH, 25 mg amorphic sucrose, 7.35 mg sodium citrate, and 0.1 mg Polysorbate (Tween) 20. The second sample contains 75 Units rFSH, 25 mg amorphic sucrose, and 0.2 mg Tween 20. The pH of both samples was adjusted to 7. The first sample is stored for 3 months at 50° C., reconstituted with purified water, and analyzed by HPSEC. The resulting profile showed little oligomer formation. The second sample, not containing sodium citrate, was stored for 6 months at 50° C., reconstituted with purified water, and analyzed by HPSEC. The resulting profile showed much more oligomer formation.

The profile of the first sample showed no degradation products while the profile of the second sample showed almost exclusively oligomeric products.

EXAMPLES II–V

Other dicarboxylic acid salt stabilizers

As depicted in FIG. 1, samples containing rFSH and various stabilizers were made, lyophilized, and tested for activity after 1 month storage at 60° C. FIG. 1 depicts the correlation between ionic strength (X 1000) of the particular stabilizer versus the percentage recovery (as determined by EIA).

The stabilizers tested were sodium citrate, both separately (II) and with 3.0 to 9.1 mg Na$_2$HPO$_4$ per ampule (III); sodium tartrate (IV); and sodium aspartate (V).

Concentrations were determined in terms of ionic strength as shown in FIG. 1.

EXAMPLE VI

The effect of weight ratio of citrate to gonadotropin (HCG) activity was tested. The results are shown in FIG. 2.

EXAMPLE VII

A lyophilised composition for recombinant human FSH was made containing 75 IU rFSH, 14.7 mg sodium citrate, 50 mg sucrose, and 0.2 mg polysorbate 20. The preparation is reconstituted with one ml of water for injection.

EXAMPLE VIII

A lyophilised composition for recombinant human FSH was made containing 75 IU rFSH, 75 IU LH, 15 mg sodium citrate, 50 mg sucrose, and 0.2 mg polysorbate 20. The composition is stable. The preparation is reconstituted with one ml of water for injection.

What is claimed is:

1. A stabilized, lyophilized human chorionic gonadotropin (HCG) composition comprising:
   one part by weight HCG and
   one to ten thousand parts by weight of at least one salt of an organic acid selected from the group consisting of salts of citric acid, tartaric acid, aspartic acid, isocitric acid and glutamic acid.

2. The stabilized HCG composition of claim 1, further comprising a non-reducing sugar selected from the group consisting of sucrose and trehalose, wherein the non-reducing sugar is present in an amount three to fifty times the amount by weight of the organic acid salt.

3. The stabilized HCG composition of claim 1, further comprising a non-ionic surfactant.

4. The stabilized HCG composition of claim 1, further comprising a second, non-HCG gonadotropin capable of stabilization by said organic acid salt.

5. A stabilized, lyophilized HCG composition comprising:
   one part by weight HCG; and
   two hundred to ten thousand parts by weigh of at least one salt of an organic acid selected from the group consisting of salts of citric acid, tartaric acid, aspartic acid, isocitric acid and glutamic acid.

6. A method of making a stabilized HCG composition comprising:
   admixing in an aqueous solution, HCG with an amount of at least one salt of an organic acid selected from the group consisting of salts of citric acid, tartaric acid, aspartic acid, isocitric acid and glutamic acid, to adjust the ionic strength of said solution to between 0.050 and 0.350; and
   dissolving a non-reducing sugar selected from the group consisting of sucrose and trehalose in said admixture in an amount of about three to fifty times the amount, by weight, of the organic acid salt; and
   freeze-drying said admixture at a temperature greater than $-35°$ centigrade to form said stabilized HCG composition.

* * * * *